United States Patent [19]

Krawzak et al.

[11] Patent Number: 5,232,664
[45] Date of Patent: Aug. 3, 1993

[54] LIQUID DISPENSER

[75] Inventors: Thomas P. Krawzak, Leominster, Mass.; Michael J. DeGroff, Tucson, Ariz.; David W. Nunnery, Tucson, Ariz.; Brian J. McGraw, Tucson, Ariz.

[73] Assignee: Ventana Medical Systems, Inc., Tucson, Ariz.

[21] Appl. No.: 762,327

[22] Filed: Sep. 18, 1991

[51] Int. Cl.$^5$ .............................................. G01N 1/14
[52] U.S. Cl. ....................... 422/64; 422/81; 422/100; 422/103; 436/54; 436/180; 73/863.57; 73/863.61; 73/864.21; 73/864.81
[58] Field of Search .............. 422/64, 68.1, 81, 100, 422/103, 104; 436/54, 180, 179; 73/863.32, 863.57, 863.61, 863.72, 864.21, 864.81

[56] References Cited

U.S. PATENT DOCUMENTS

| | | | |
|---|---|---|---|
| 3,572,130 | 3/1971 | Goldsmith | 73/425.6 |
| 3,754,687 | 8/1973 | Norton | 222/309 |
| 3,817,425 | 6/1974 | Liston | 222/1 |
| 3,831,618 | 8/1974 | Liston | 137/154 |
| 3,955,930 | 5/1976 | Shapiro | 23/259 |
| 4,011,685 | 3/1977 | Boyd et al. | 422/100 |
| 4,372,175 | 2/1983 | Parker | 73/864.17 |
| 4,429,583 | 2/1984 | Watanabe et al. | 73/864.12 |
| 4,526,294 | 7/1985 | Hirschmann et al. | 222/47 |
| 4,601,212 | 7/1986 | Shapiro | 73/864.18 |
| 4,690,005 | 9/1987 | Tervamäki et al. | 73/864.12 |
| 4,760,939 | 8/1988 | Ball et al. | 422/100 |
| 4,810,659 | 3/1989 | Higo et al. | 436/180 |
| 4,818,706 | 4/1989 | Starr | 436/180 |
| 4,844,868 | 7/1989 | Kokugawa | 422/64 |
| 4,868,129 | 9/1989 | Gibbons et al. | 436/180 |

Primary Examiner—Lynn M. Kryza
Attorney, Agent, or Firm—Skjerven, Morrill, MacPherson, Franklin & Friel

[57] ABSTRACT

A dispenser which can deliver precise small amounts of a liquid is disclosed. The dispenser is particularly suited to applying reagents in a biological test such as an immunoassay. It includes a reservoir chamber linked to a dispense chamber via a check valve, the two chambers preferably being in the form of syringes. An outlet line leading from the dispense chamber to a nozzle includes a delay check valve (preferably a ball inside a cylindrical chamber) which allows continuous outward flow, but shuts off flow in the reverse direction after allowing a predetermined volume to pass. The process of refilling the dispense chamber from the reservoir chamber creates reverse flow in the nozzle and causes a hanging drop of liquid at the tip of the nozzle to be withdrawn.

30 Claims, 8 Drawing Sheets

LIQUID DISPENSER

FIELD OF THE INVENTION

This invention relates to devices which dispense a measured volume of a liquid and, in particular, to liquid dispensers which provide a precise small volume of a liquid reagent used in conducting a biological test such as an immunoassay.

BACKGROUND OF THE INVENTION

In performing biological tests and analyses, it is often necessary to dispense a series of liquids such as reagents into a test area, e.g., a slide. For example, in an immunoassay of tumor tissue, a thinly sliced section of the tissue is placed on a slide, rinsed and covered with an evaporation inhibitor. Then a measured amount of a primary antibody solution (e.g., 100 $\mu$l) is dispensed onto the slide. The antibody solution passes through the evaporation inhibitor and comes into contact with the tissue section. The primary antibody and rinse solution remaining on the slide (e.g., ~300 $\mu$l) are mixed, by directing a stream of air onto the slide, and are incubated for a period of time. The slide is washed and the process is repeated with an enzyme-labeled secondary antibody solution. After another washing, an enzyme substrate solution (indicator), a color enhancer, and a counterstain are added to the slide in sequence. Before each of these liquids is added, the slide is washed and a fresh layer of evaporation inhibitor is applied.

In a process such as the foregoing, many of the reagents must be deposited on the slide in precisely measured small amounts (often expressed in $\mu$l). The process is highly labor intensive and can be variable if performed manually, and therefore a number of devices have been proposed for automating all or a portion of the process.

Application Ser. No. 07/488,601, filed Mar. 2, 1990 co-owned with this application and incorporated herein by reference, describes a reagent carousel which cooperates with a slide support carousel to apply a sequence of preselected reagents to each of the slides with interposed mixing, incubating and rinsing steps. The reagent carousel holds a plurality of reagent containers and includes a drive means for positioning the appropriate reagent container over one of the slides in the slide carousel. Air cylinder or equivalent actuators make contact with the individual reagent containers and thereby cause reagent to be delivered on to the slides.

The reagent container described in the above-mentioned application Ser. No. 07/488,601 is a small bottle capped with a microdelivery pump/valve. After the pump/valve is primed, the bottle is inverted and placed on the carousel above the slide area. The actuator is positioned above the bottle and, when activated, forces the bottle downward, dispensing a predetermined volume of reagent.

Liquid dispensing arrangements such as this have several limitations. First, they frequently include a metal compression spring in the path of the fluid. The metal spring may react with several of the liquids dispensed (e.g., salts), and metal ions which enter the reagent may act as a catalyst for redox reactions which will destabilize indicators and proteins and will create problems with the specific chemical reactions, generally causing a loss of activity and a loss in sensitivity of the assays. Second, the bottle is not vented and develops an internal vacuum as the reagent is dispensed. To avoid generating a complete vacuum, the bottles are normally only half filled. Third, a certain amount of air remains in the pump chamber after the priming process. This air may deflect the reagent stream sideways or cause it to spray out of the nozzle during the initial dispensing operations, causing the volume of liquid delivered to be unpredictable. Moreover, as the pressure inside the bottle falls during succeeding dispensing operations, this air migrates toward the interior of the bottle, causing the volume of liquid dispensed to increase. Fourth, a drop of liquid forms at the tip of the nozzle after each dispensing operation, and may fall off as the carousel rotates. This can create problems if, for example, the drop lands on another slide. Finally, some of the bottles must be opaque to protect photosensitive reagents, and the operator is unable to tell how much reagent remains in the bottle.

The liquid dispenser of this invention overcomes all of these problems.

SUMMARY OF THE INVENTION

A liquid dispenser according to this invention includes two chambers: a dispense chamber and a reservoir chamber. The chambers are connected by a supply line, which includes a check (one-way) valve, allowing fluid to flow only from the reservoir chamber to the dispense chamber. A dispense line connects the dispense chamber to a nozzle, from which the liquid is dispensed.

The dispense line includes a delay check valve. The delay check valve allows fluid to flow in an unrestricted volume from the dispense chamber to the nozzle. In the other direction, however, the delay check valve allows only a predetermined volume of fluid to flow before it closes, restricting all further flow from the nozzle to the dispense chamber. The next dispense from the dispense chamber to the nozzle opens the delay check valve again, allowing an additional amount of fluid to flow in the reverse direction and causing it to close again.

In one embodiment, the delay check valve comprises a ball enclosed in a cylindrical chamber. The diameter of the ball chamber is slightly larger than the diameter of the ball, allowing the ball to move freely along the length of the chamber. At the inlet to the ball chamber from the dispense chamber, the surface of the port is shaped to allow the ball to seat and thereby prevent flow in the direction of the dispense chamber. At the outlet from the ball chamber, no such seating surface is provided and thus fluid may flow downstream toward the nozzle even when the ball is pressed against the outlet. When fluid is dispensed from the nozzle, the ball is forced against the outlet from the ball chamber. If the direction of flow in the dispense line is reversed, the ball moves in the opposite direction until it seats against the inlet port to the ball chamber. Further flow toward the dispense chamber then ceases.

In operation, a measured amount of liquid is forced from the dispense chamber and out through the nozzle. A means is provided for drawing a new volume of liquid into the dispense chamber. Since a small threshold pressure differential is necessary to draw liquid in the forward direction through the check valve linking the reservoir chamber and the dispense chamber, liquid is initially drawn into the dispense chamber through the nozzle, where there is essentially no resistance. This continues until the ball has seated against the inlet to the ball chamber, cutting off further reverse flow. From this point, fluid flows from the reservoir chamber to the dispense chamber until the dispense chamber has been refilled.

In an alternative embodiment, the check valve between the reservoir chamber and the dispense chamber is omitted, and a resistance to flow from the reservoir chamber to the dispense chamber is provided by alternative means, such as a constricted section in the supply line.

In a preferred embodiment, both the reservoir chamber and the dispense chamber are cylindrical in shape and oriented vertically. The reservoir chamber contains a piston which contacts the top surface of the liquid in that chamber and slides freely as the volume of liquid in the chamber decreases. The dispense chamber includes a piston and a plunger mechanism for forcing fluid from the chamber. An external compression spring (which does not contact the liquid) returns the plunger to its retracted position after each dispensing operation.

In another embodiment, a check valve replaces the piston in the reservoir chamber.

The liquid dispenser of this invention can be constructed so that only non-metallic materials come into contact with the liquid. The dispenser can be primed quickly and easily, and no air remains in any pump chamber or valve after it is primed. Even if the dispenser is made of opaque materials, the amount of liquid remaining can easily be determined by detecting the position of the piston in the reservoir chamber. After each dispensing operation, the dispenser automatically withdraws the drop remaining on the tip of the nozzle. The entire dispenser can be made of plastic and can be disposable.

In another aspect of this invention, the dispenser is provided with a spring-loaded mechanism, which allows it easily to be inserted into and removed from a reagent tray. The reagent tray is removably engaged to a drive carousel by a number of interlocking teeth.

DESCRIPTION OF THE INVENTION

Figure 1:
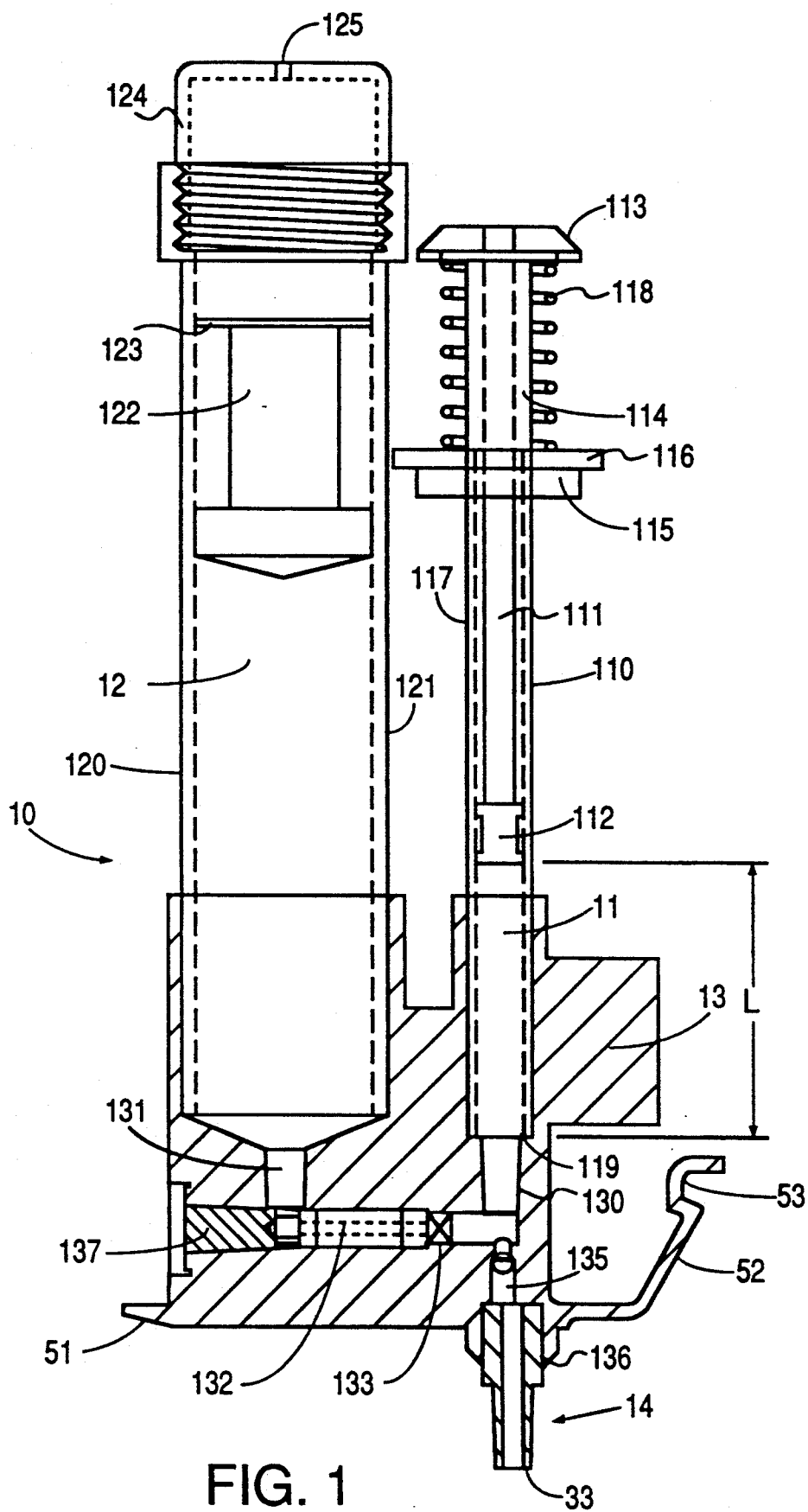
FIG. 1 is an elevational cutaway view of a dispenser in accordance with the invention.

A preferred embodiment of the invention is illustrated in FIG. 1. A liquid dispenser 10 includes a dispense chamber 11, a reservoir chamber 12, a coupling block 13 and a nozzle 14. Dispense chamber 11 is included in a syringe 110, and reservoir chamber 12 is included in syringe 120. Syringe 110 and syringe 120 have tapered ends which are fitted snugly into receiving holes 130 and 131, respectively, which are formed in coupling block 13.

Syringe 110 includes a plunger 111 terminating in a piston 112, which slides along the inside surface of syringe 110. The other end of plunger 111 terminates in a cap 113. A pair of side walls 114 extend downward from cap 113 and end in an annular ring 115. The top surface of annular ring 115 engages a stop 116, which is connected to a barrel 117 of syringe 110. A compression spring 118 presses against the lower surface of cap 113 and the upper surface of stop 116, thereby forcing annular ring 115 against stop 116 and maintaining piston 112 in its uppermost position.

Figure 2:
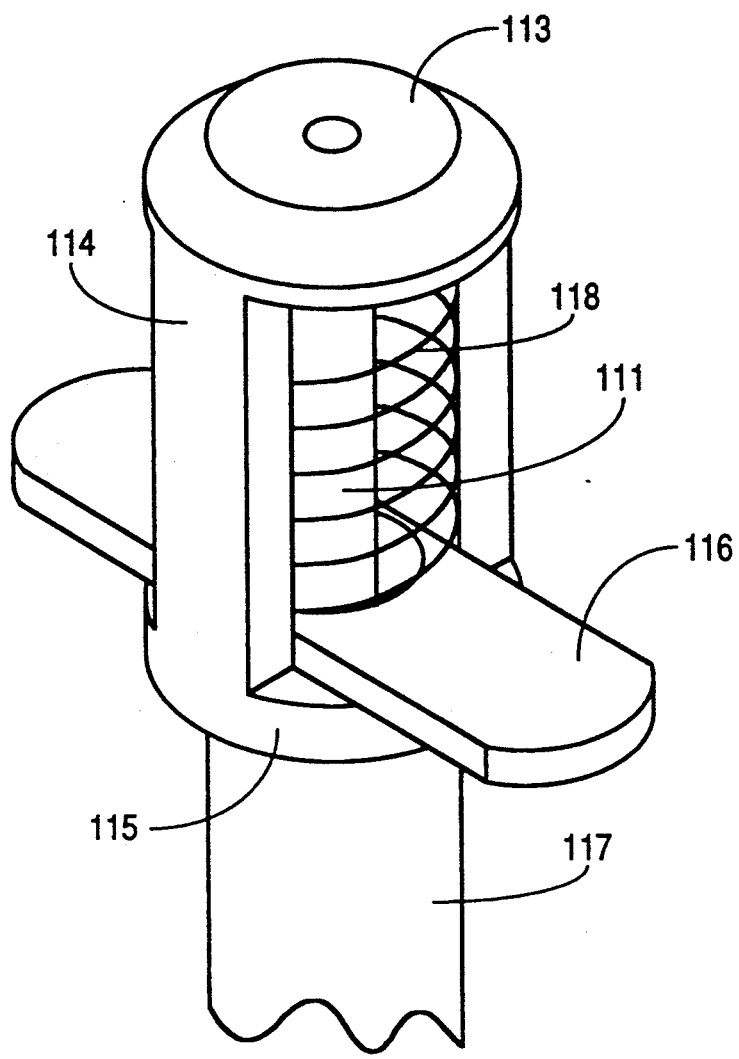
FIG. 2 is a perspective view of a portion of the dispenser shown in FIG. 1.

The elements near the top of syringe 110 are shown in perspective in FIG. 2.

Liquid is ejected from dispense chamber 11 by exerting a downward force on cap 113, against the force of compression spring 118. This forces piston 112 downward until it reaches point 119, where it is prevented by the tapered portion of syringe 110 from further downward movement. Thus, the total volume of liquid expelled from dispense chamber 11 is equal to the inside cross-sectional area of barrel 117 multiplied by the vertical displacement of piston 112, shown as L in FIG. 1.

When liquid dispenser 10 is mounted on a reagent tray, as described below, the downward force on cap 113 is applied by an actuator driven by an air cylinder or some other means.

Syringe 120 is larger than syringe 110, but it has a similar tapered portion which is inserted into coupling block 13 in the same manner as syringe 110. Syringe 120 includes a barrel 121 within which a piston 122 slides. Piston 122 includes a guide portion 123, which ensures that piston 122 remains properly oriented within barrel portion 121 to prevent the leakage of liquid from reservoir chamber 12. Piston 122 slides freely within syringe 120 so that its position indicates the top surface of liquid within reservoir chamber 12. Syringe 120 has a removable cap 124 which is screwed on to barrel 121 and is provided with an aperture 125 for allowing air to enter the space above piston 122. If syringe is required to be opaque, the position of piston 122 can be viewed by removing cap 124.

A supply line 132 is formed in coupling block 13 and connects the tapered outlet ports of syringes 110 and 120. A check valve 133, preferably of the "duck bill" variety, is inserted in supply line 132 and oriented so as to allow flow in the direction from reservoir chamber 12 to dispense chamber 11. The outlet of syringe 110 is aligned with a ball chamber 135. At the lower terminus of ball chamber 135 a cylindrical hole 136 is bored in coupling block 13 into which nozzle 14 is snugly fitted. An open end of supply line 132 is sealed off by plug and supply line assembly 137. Plug and supply line assembly 137 seals a hole formed in coupling block 13 and routes a fluid from the outlet part of syringe 120 through check valve 133.

Figure 3:
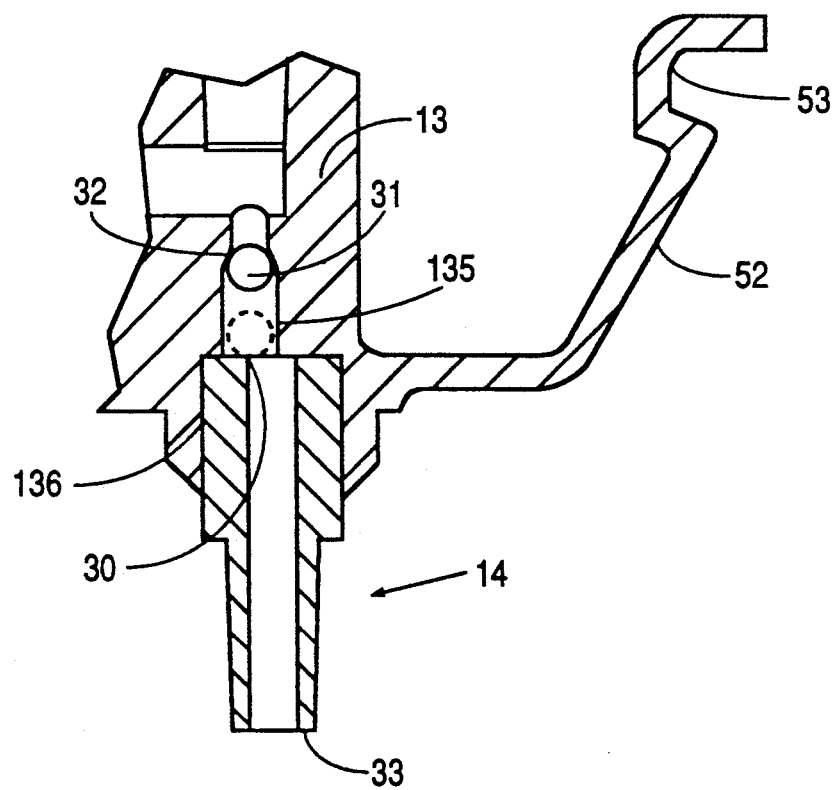
FIG. 3 is a detailed view of the ball chamber and nozzle.

The details of ball chamber 135 and nozzle 14 are illustrated in FIG. 3. Hole 136 bored in coupling block 13 is offset from ball chamber 135 so that an inner edge 30 of nozzle 14 protrudes into the outlet of ball chamber 135. Nozzle 14 has a tip 33. Ball chamber 135 contains a ball 31 which fits loosely against the cylindrical surface of ball chamber 135 and is free to move between an uppermost position (shown by a solid line in FIG. 3) and a lowermost position (shown by a hatched line in FIG. 3). In its uppermost position, ball 31 mates with the surface of an inlet port 32 of ball chamber 135, thereby preventing liquid flow in the direction from nozzle 14 to dispense chamber 11. At its lowermost position, ball 31 is restrained by inner edge 30 of nozzle 14 and prevented from falling into nozzle 14. This does not prevent liquid from flowing from ball chamber 135 to nozzle 14, however.

Using the above described structure as a basis, the operation and unique characteristics of dispenser 10 will now be described. At the beginning of a dispense stroke, plunger 111 and piston 112 are in the positions shown in FIG. 1. When liquid is to be dispensed, a downward force is applied against cap 113. This overcomes the force of compression spring 118 and forces piston 112 downward until it reaches point 119, thereby dispensing a predetermined volume of liquid equal to the distance L multiplied by the internal cross-sectional area of barrel 117. The liquid flows from dispense chamber 11 into ball chamber 135. It cannot flow into supply line 132 because check valve 133 is oriented so as to prevent flow towards reservoir chamber 12. The downward flow through ball chamber 135 forces ball 31 to its lowermost position, abutting edge 30, but this does not prevent flow in this direction and the measured amount of liquid is ejected from nozzle 14. Normally, the surface tension of the liquid leaves a drop hanging at tip 33 of nozzle 14, so that the volume of liquid actually reaching its intended destination is equal to the volume of dispense chamber 11, less the volume of liquid in the hanging drop.

When plunger 111 has reached its lower extreme position, the downward force on cap 113 is released, and compression spring 118 takes over, forcing Cap 113 in an upward direction. Plunger 111 and piston 112 also move in this direction, and liquid begins to be sucked into dispense chamber 11.

It is here that the interplay of check valve 133 and ball chamber 135 becomes important. Check valve 133 is a duck bill valve, which requires a predetermined threshold pressure differential in order to permit flow in the forward direction. In contrast, ball 31 moves freely within ball chamber 135, and therefore provides essentially no resistance to liquid flow from nozzle 14 until it reaches its sealing position at inlet port 32. When the dispense operation is completed, the liquid flow has forced ball 31 to its lowermost position, abutting edge 30. As the upward movement of piston 112 begins to draw liquid back into dispense chamber 11, the upward flow of fluid in ball chamber 135 pulls ball 31 upward until it reaches port 32, where it cuts off any further liquid flow toward dispense chamber 11. Until ball 31 reaches point 32, however, there is virtually no resistance to liquid flow from nozzle 14, and therefore no pressure differential is created across duck bill check valve 132 sufficient to cause liquid flow from reservoir chamber 12 to dispense chamber 11.

The volume of liquid which flows from nozzle 14 towards dispense chamber 11 while ball 31 is moving from its lowermost to its uppermost position is preselected to be a volume exactly equal to the volume of the hanging drop left at tip 33 at the end of the dispense cycle. Thus, the drop is effectively drawn back into nozzle 14 and an internal meniscus forms at tip 33.

When ball 31 reaches port 32, it shuts off further flow from nozzle 14 into dispense chamber 11. This immediately creates a pressure differential across check valve 133 and causes liquid to flow from reservoir chamber 12 into dispense chamber 11. The suction generated in dispense chamber 11 keeps ball 31 firmly seated against port 32 and prevents any further flow from nozzle 14.

When compression spring 118 has forced annular ring 115 against stop 116, syringe 110 is returned to its original condition and is ready for another dispense cycle. Ball 31, being made of a material slightly more dense than the liquid, falls through ball chamber 135 until it makes contact again with edge 30.

Figure 4:
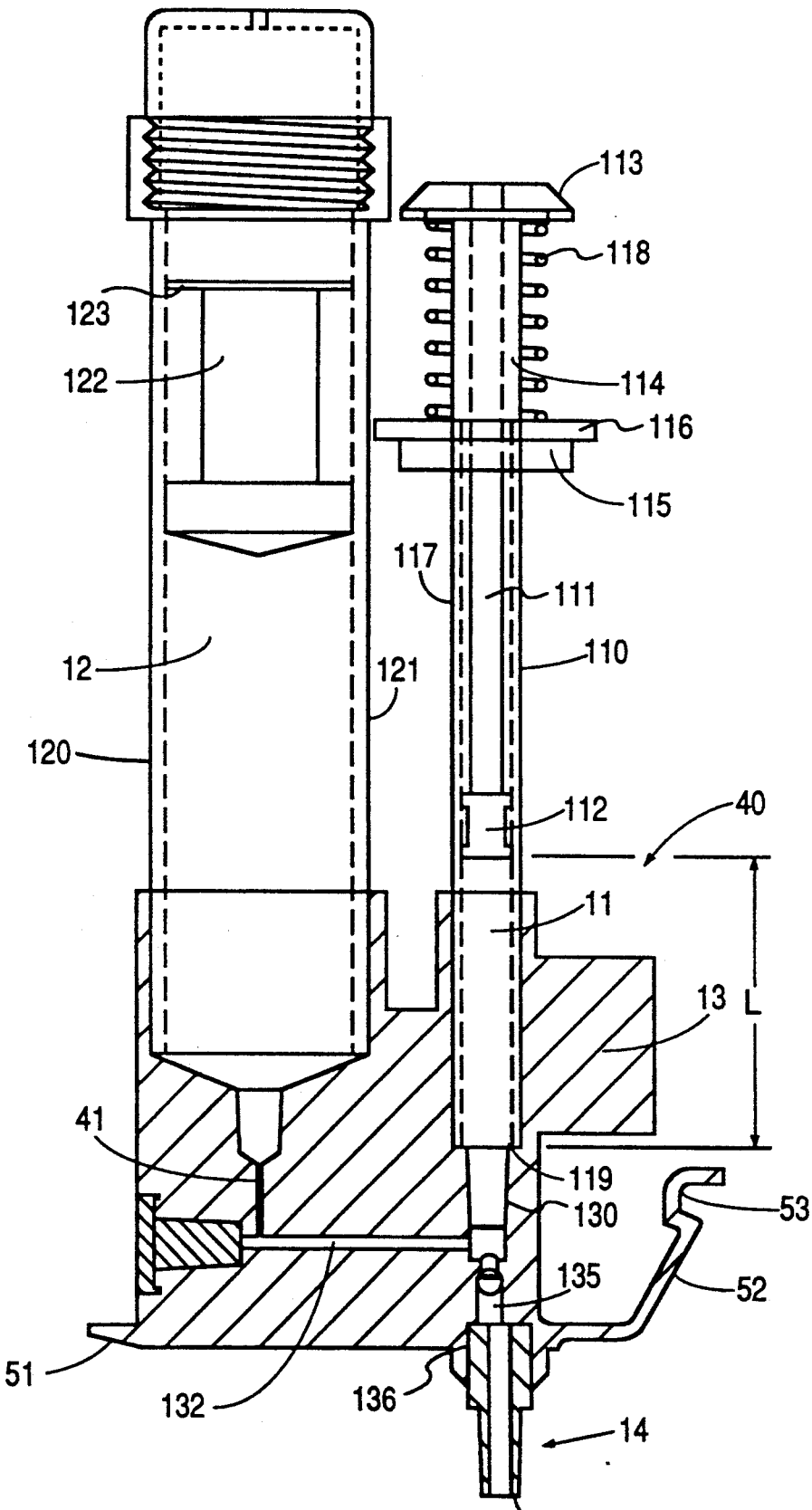
FIGS. 4 and 5 are elevational cutaway views of additional embodiments in accordance with the invention.

A simplified "one-valve" embodiment of this invention is illustrated in FIG. 4. Liquid dispenser 40 is identical to liquid dispenser 10 except that check valve 133 has been omitted and has been replaced by a constricted section 41 in supply line 132. Otherwise, all of the elements of liquid dispenser 40 are identical to those in liquid dispenser 10 and are similarly numbered.

The dispense operation begins with a downward force on cap 113, preferably supplied by an actuator driven by an air cylinder. Piston 112 moves downward, forcing liquid from dispense chamber 11. As in the case of liquid dispenser 10, liquid flows through ball chamber 135 and out nozzle 14. In this case, however, since there is no check valve in supply line 132, a small portion of liquid flows through supply line 132 and into reservoir chamber 12. Two factors limit the volume of this flow: (i) the constricted section 41 in supply line 132; and (ii) the friction between piston 122 and the walls of syringe 120. The combined resistance provided by these two factors is significantly greater than the resistance in nozzle 14, and therefore the amount of flow into reservoir chamber 12 is minimal. Moreover, the volume of flow into reservoir chamber 12 can be determined in advance by testing, and it is taken into account in determining the volume of liquid that will be dispensed.

When the dispense cycle is completed, compression spring 118 forces cap 113 upward, drawing liquid back into dispense chamber 11. Liquid flows into dispense chamber 11 from nozzle 14 and supply line 132. Initially, however, the flow from nozzle 14 is substantially greater than the flow from supply line 132, owing to the resistance provided by constricted section 41 in supply line 132. When ball 31 seats at the inlet port 32 to ball chamber 135, however, flow from nozzle 14 ceases, and the remaining flow into dispense chamber 11 comes from reservoir chamber 12. In the same manner as in liquid dispenser 10, the drop hanging from nozzle 14 is withdrawn, and a meniscus forms at the tip 33 of nozzle 14.

Figure 5:
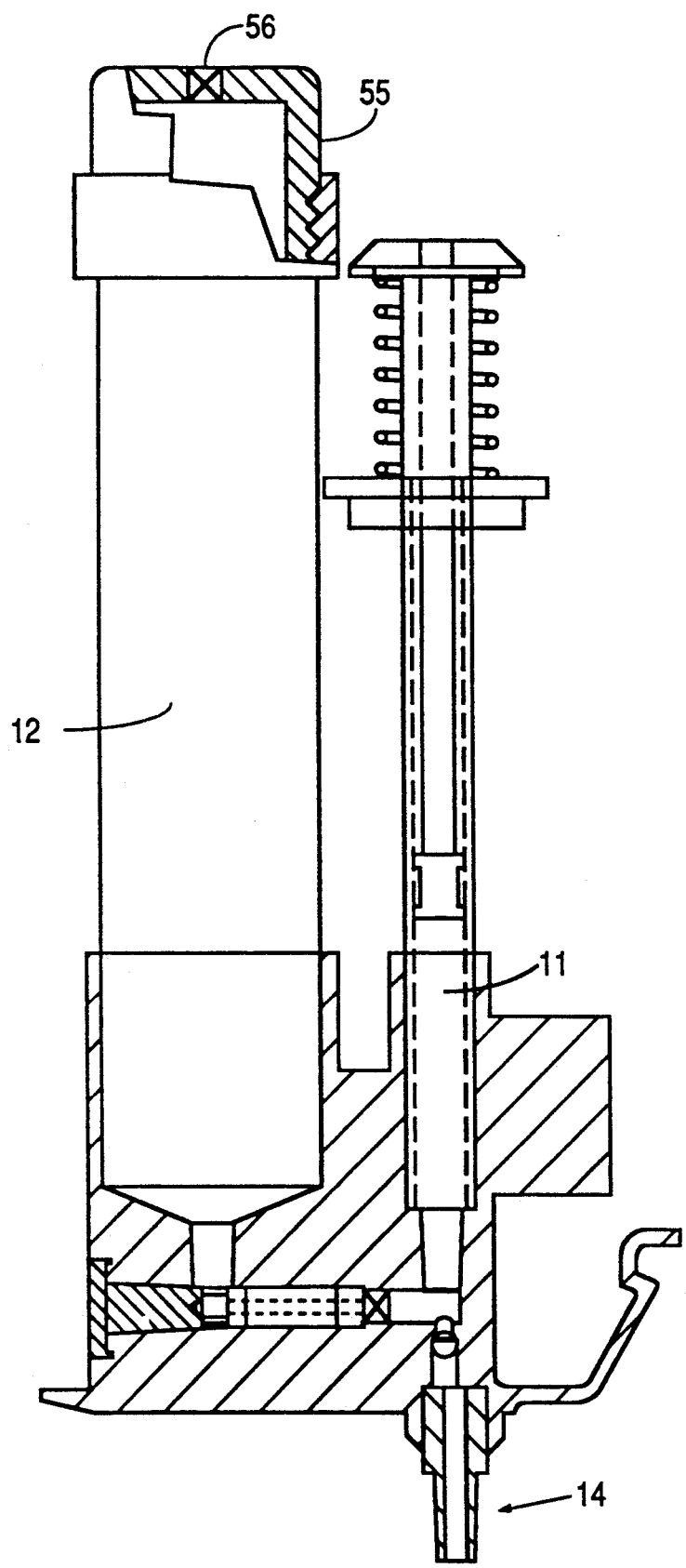

An alternative structure for reservoir chamber 12 is shown in the embodiment of FIG. 5. In this embodiment the aperture in cap 55 is provided with a check valve 56 which allows air to flow into reservoir chamber 12. Piston 122 and guide 123 are omitted.

As described in the above-mentioned application Ser. No. 07/488,601, liquid dispenser 10 preferably has a bar code affixed to it which identifies the liquid which it contains. Liquid dispenser 10 is placed in a reagent tray and a bar code reader and homing system are provided for reading the bar code and indexing the position of liquid dispenser 10 on the reagent tray.

Figure 8:
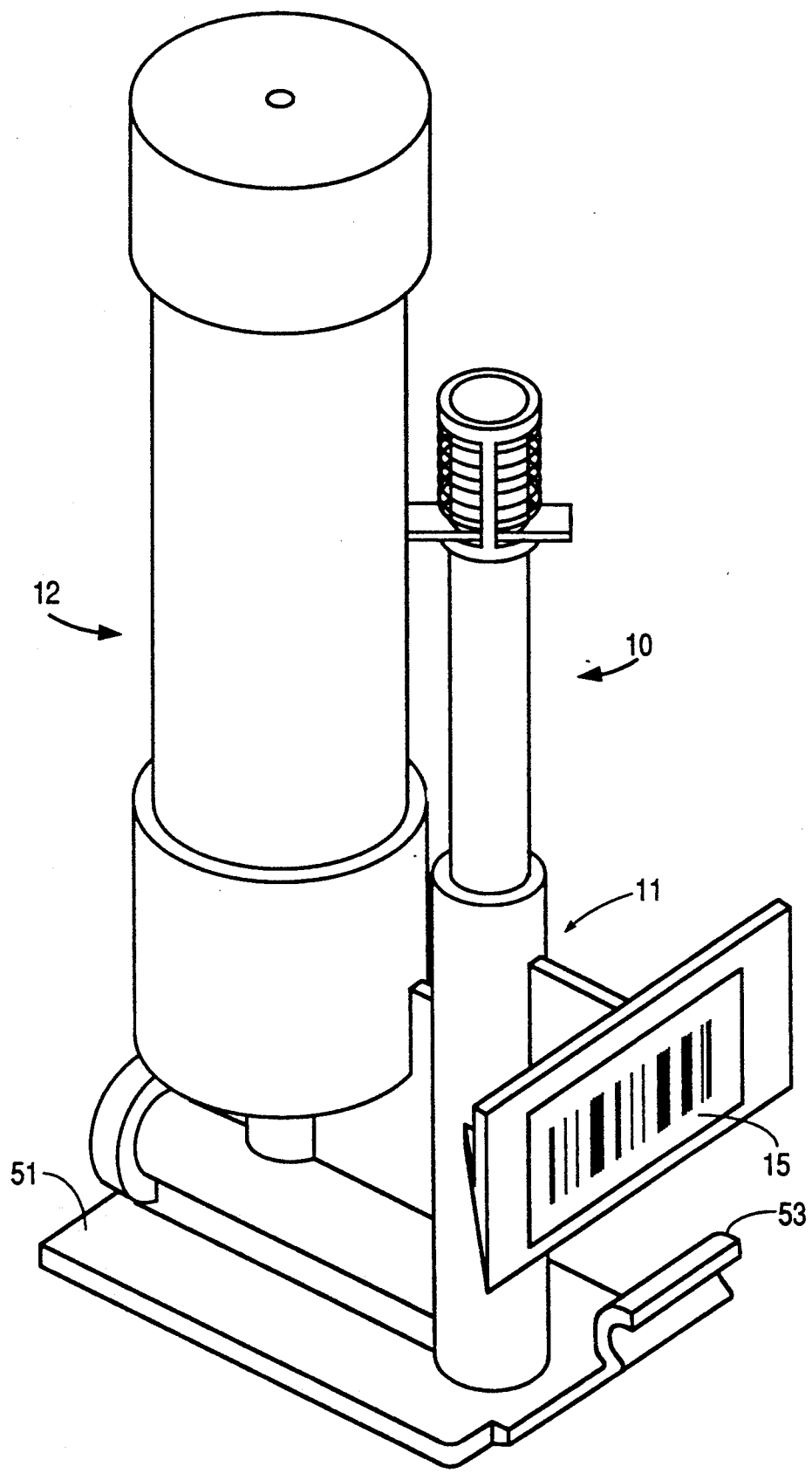
FIG. 8 is a perspective view of a liquid dispenser according to the invention.

For the system to work effectively, liquid dispenser 10 must be mounted securely and firmly on the reagent tray to assure that the bar code may be properly read. An illustrative position for a bar code 15 is shown in FIG. 8.

It is also important that liquid dispenser 10 be easily mounted on and removed from the reagent tray. As shown in FIG. 1, liquid dispenser 10 includes a foot 51 and a spring member 52, which has a groove 53.

Figure 6:
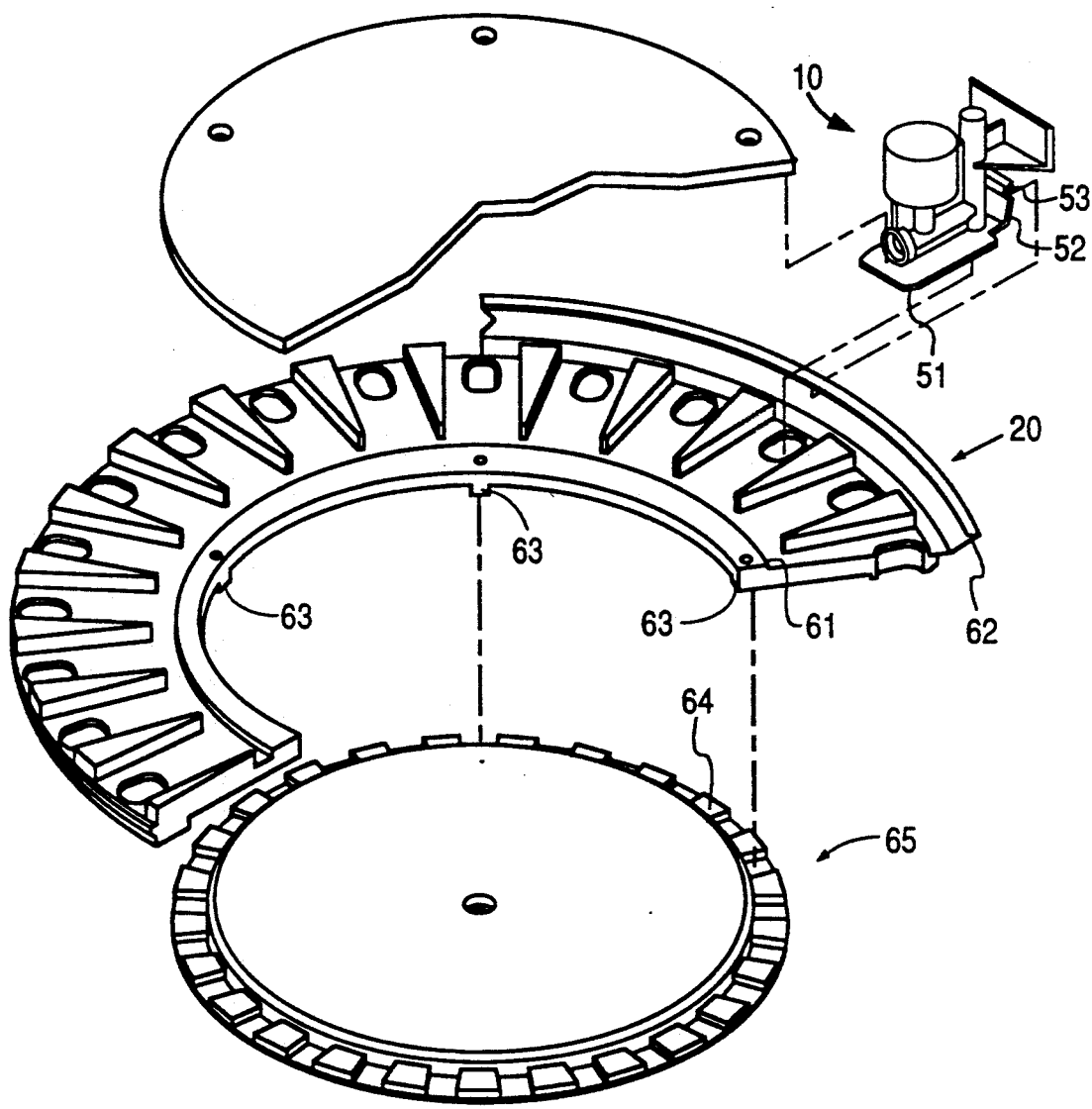
FIGS. 6 and 7 illustrate the mounting of a liquid dispenser on a reagent tray and the manner in which a reagent tray is engaged with a drive carousel.
Figure 7:
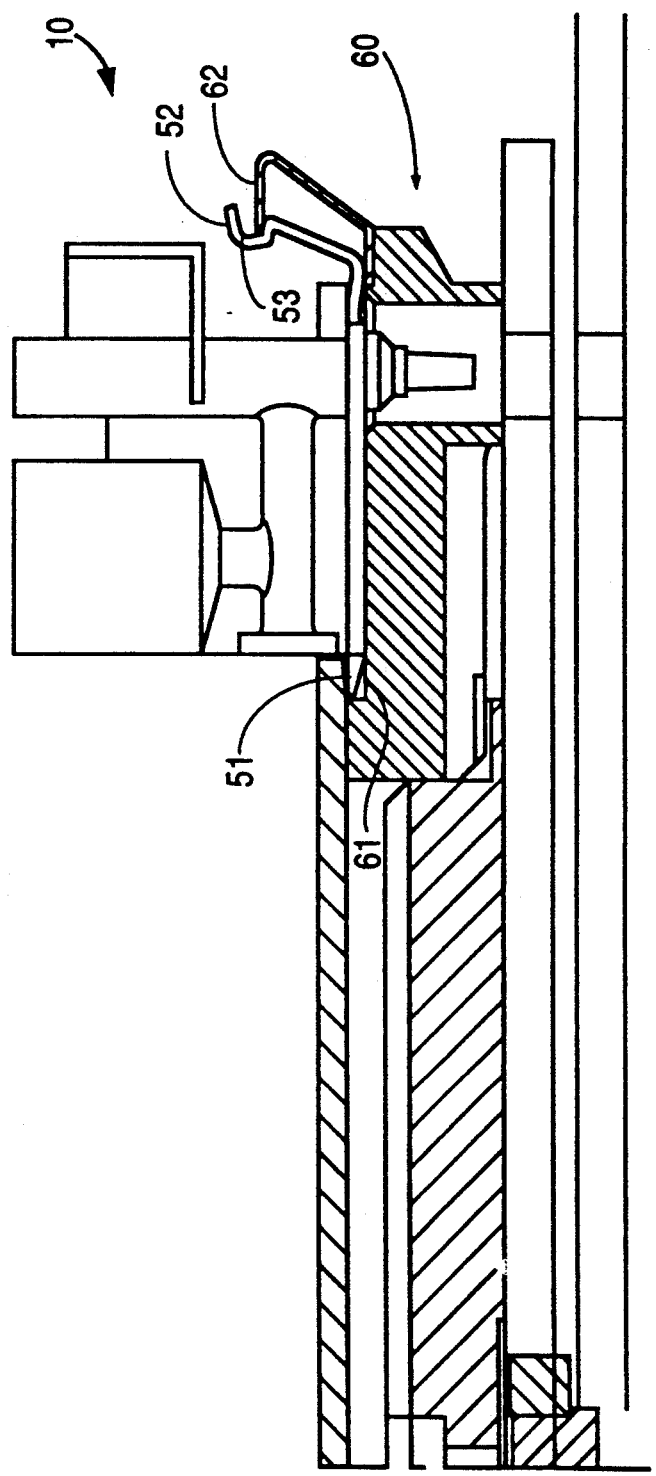

FIGS. 6 and 7 illustrate the manner of mounting liquid dispenser 10 in a reagent tray 60. Foot 51 is initially inserted into a circular U-shaped groove 61 formed in reagent tray 60. Groove 53 of spring member 52 engages a circumferential lip 62 of tray 60.

FIG. 7 shows a cross-sectional view of liquid dispenser 10 after it has been mounted on reagent tray 60, showing in particular the manner in which foot 51 fits into groove 61 and showing the flexing of spring member 52 to hold dispenser 10 firmly in place.

To remove liquid dispenser 10, spring member 52 is simply bent inward slightly so that groove 53 clears lip 62, and foot 51 is withdrawn from groove 61.

Normally, a reagent tray containing a number of liquid dispensers is refrigerated when it is not in use. Therefore, the reagent tray must be readily removable from the testing apparatus so that it can be placed in a refrigerator. As shown in FIG. 6, reagent tray 60 has a plurality of teeth 63 which mate with corresponding teeth 64 in a drive carousel 65, which is driven by a stepper motor (not shown), for example. When reagent tray 60 is to be refrigerated, it is simply lifted from drive carousel 65. When it is to be placed back in use, it is placed on drive carousel 65, the teeth 63 meshing with the teeth 64. It is not necessary to orient reagent tray 60 in the same angular position as it was when it was removed, since the bar code reader and homing system will quickly determine the location of each reagent on reagent carousel tray 60.

The disclosures of the foregoing embodiments are intended to be illustrative and not limiting. Accordingly, many other embodiments will be apparent to those skilled in the art, all of which are intended to be within the broad scope of this invention.

We claim:

1. A liquid dispenser comprising:
    a reservoir chamber;
    a dispense chamber;
    a supply channel connecting the reservoir chamber and the dispense chamber, the supply channel containing a means for providing a resistance to flow between the reservoir chamber and the dispense chamber;
    a dispense channel extending from the dispense chamber and terminating at an orifice for delivering a fluid from the liquid dispenser, the dispense channel containing a delay check valve means, the delay check valve means operative to allow a continuous flow of liquid from the dispense chamber and out through the orifice and to allow a predetermined volume of liquid to flow from the orifice and into the dispense chamber, shutting off flow of liquid towards the dispense chamber after the predetermined volume of liquid has entered the dispense chamber; and
    means to expel liquid from the dispense chamber through the dispense channel.

2. The liquid dispenser of claim 1 wherein the means for providing a resistance of flow comprises a check valve, the check valve being oriented so as to prevent liquid flow into the reservoir chamber.

3. The liquid dispenser of claim 2 wherein the check valve is a duckbill valve.

4. The liquid dispenser of claim 1 wherein the means for providing a resistance to flow comprises a conduit having an inside diameter sized to provide a significant resistance to flow through the conduit.

5. The liquid dispenser of claim 1 wherein the delay check valve means comprises a body positioned within a chamber, the chamber having an inlet port and an outlet port, the body being sized and shaped so as to mate with a surface adjacent the inlet port and thereby shut off flow towards the dispense chamber, the body being free to move away from the surface so as to permit liquid flow from the dispense chamber.

6. The liquid dispenser of claim 5 wherein the body is spherical in shape.

7. The liquid dispenser of claim 6 wherein the chamber comprises a cylindrical wall.

8. The liquid dispenser of claim 1 comprising a means to draw liquid into the dispense chamber.

9. The liquid dispenser of claim 8 wherein said dispense chamber comprises a cylindrical wall and the means to expel liquid and the means to draw liquid comprise a piston slidably disposed within the cylindrical wall.

10. The liquid dispenser of claim 9 wherein the dispense chamber and the means to expel liquid and means to draw liquid comprise a syringe.

11. The liquid dispenser of claim 9 in combination with a pneumatically driven actuator for actuating a plunger in the syringe.

12. The liquid dispenser of claim 1 wherein the reservoir chamber comprises a cylindrical wall and a piston is slidably disposed in the wall.

13. The liquid dispenser of claim 1 wherein the reservoir chamber comprises a check valve for admitting air into the reservoir chamber.

14. The liquid dispenser of claim 1 comprising a means for removably mounting the liquid dispenser on a reagent tray.

15. The liquid dispenser of claim 14 having a bar code applied to a surface thereof.

16. The liquid dispenser of claim 14 wherein said means for removably mounting the liquid dispenser comprises a foot and a spring member, the foot to be inserted in a groove in the tray and the spring member to engage a corresponding part of the tray when the dispenser is mounted on the tray.

17. The liquid dispenser of claim 16 wherein the spring member comprises a groove for engagement with a lip on the tray.

18. A combination comprising:
    the liquid dispenser of claim 17; and
    a reagent tray comprising a groove and a lip, the foot of the liquid dispenser being inserted in the groove of the tray and the groove in the spring member engaging a lip on the reagent tray.

19. The combination of claim 18 wherein the reagent tray, the groove therein, and the lip are circular in shape.

20. The combination of claim 19 wherein the liquid dispenser has a bar code applied to a surface thereof, the bar code being readable by a bar code reader for identifying the contents of the liquid dispenser.

21. The combination of claim 19, the reagent tray comprising a plurality of teeth for meshing with a plurality of corresponding teeth in a drive carousel.

22. A combination comprising:
    the combination of claim 21; and
    a drive carousel, the teeth of the reagent tray meshing with corresponding teeth in the drive carousel.

23. A liquid dispenser for dispensing reagents for use in biological tests, the liquid dispenser comprising a foot and a spring member for removably mounting the liquid dispenser in a reagent tray, the foot to be inserted in a groove in the tray and the spring member to engage a corresponding part of the tray when the dispenser is mounted in the tray.

24. The liquid dispenser of claim 23 wherein the spring member comprises a groove for engagement with a lip on the tray.

25. A combination comprising:
   the liquid dispenser of claim 24; and
   a reagent tray comprising a groove and a lip, the foot of the liquid dispenser being inserted in the groove of the tray and the groove in the spring member engaging a lip on the reagent tray.

26. The combination of claim 25 wherein the reagent tray, the groove therein, and the lip are circular in shape.

27. The combination of claim 26, the reagent tray comprising a plurality of teeth for meshing with a plurality of corresponding teeth in a drive carousel.

28. A combination comprising:
   the combination of claim 27; and
   a drive carousel, the teeth of the reagent tray meshing with corresponding teeth in the drive carousel.

29. A liquid dispenser comprising:
   a reservoir chamber;
   a dispense syringe;
   a supply line linking the reservoir chamber and the dispense syringe, the supply line containing a check valve for allowing liquid flow in the supply line only from the reservoir chamber to the dispense syringe; and
   a dispense line extending from the dispense syringe to a nozzle, said dispense line containing a cylindrical ball chamber in flow communication with the dispense syringe, the ball chamber having a ball retained therein and comprising an inlet port with an adjacent surface for mating with the ball so as to prevent liquid flow into the dispense chamber, the ball chamber allowing continuous liquid flow form the dispense chamber.

30. The liquid dispenser of claim 29 wherein the check valve comprises a duckbill valve.

* * * * *